(12) United States Patent
Masatoki et al.

(10) Patent No.: US 6,758,108 B2
(45) Date of Patent: Jul. 6, 2004

(54) SOLDERABILITY TESTING APPARATUS AND SOLDERABILITY TESTING METHOD (75) Inventors: Tamiharu Masatoki, Tokyo (JP); Yutaka Shinozaki, Saitama (JP)

(73) Assignee: Sony Corporation, Tokyo (JP)

( * ) Notice: Subject to any disclaimer, the term of this patent is extended or adjusted under 35 U.S.C. 154(b) by 158 days.

(21) Appl. No.: 10/080,132

(22) Filed: Feb. 21, 2002

(65) Prior Publication Data

US 2002/0157486 A1 Oct. 31, 2002

(30) Foreign Application Priority Data

Feb. 27, 2001 (JP) .................................... P2001-051611

(51) Int. Cl.[7] .............................................. G01N 13/02
(52) U.S. Cl. ...................... 73/866; 228/103; 73/53.01
(58) Field of Search ............................... 73/53.01, 866, 73/826, 862.541, 53.4; 228/103

(56) References Cited

U.S. PATENT DOCUMENTS 4,420,110 A     12/1983 McCullough et al.
4,962,905 A     10/1990 Friend et al.
5,001,923 A      3/1991 Schmitt-Thomas
5,100,701 A      3/1992 Freller et al.

FOREIGN PATENT DOCUMENTS

JP      07072064        3/1995
JP       0749009       12/1996

*Primary Examiner*—Robert Raevis
(74) *Attorney, Agent, or Firm*—Sonnenschein, Nath & Rosenthal LLP (57) ABSTRACT This invention discloses a solderability testing apparatus which comprises a sample parts holding means having a sample parts holding member for holding a sample; an external force detection means for supporting such sample parts holding means; a solder paste container for containing a solder paste which is internally added with a flux; and a heating means for heating the solder paste; wherein such apparatus has a flux wetting preventive layer at least on the surface of a sample holding portion of the sample parts holding member.

16 Claims, 7 Drawing Sheets

SOLDERABILITY TESTING APPARATUS AND SOLDERABILITY TESTING METHOD

CROSS REFERENCES TO RELATED APPLICATIONS

The present invention claims priority to priority document no. 2001-051611 filed in Japan on Feb. 27, 2001, and incorporated by reference herein.

BACKGROUND OF THE INVENTION

1. Field of the Invention

The present invention relates to a solderability testing apparatus and a solderability testing method.

2. Description of the Related Art

To achieve a desirable soldering, enough metallic bonding should be formed between a metal composing a base material (e.g. copper foil (or land portion) on printed circuit boards, and electrode portion of surface mounted devices) and solder (which is generally made of an alloy of tin and lead. It is thus necessary to ensure wetting of the surface of the base material with the solder (more specifically, tin). The wetting solder (tin) diffuses into the base material and forms therein an alloy layer formed with such base material through metallic bond, which is a final form of the soldering. So that testing the wetting balance between the base material and the solder can provide a quantitative evaluation of solderability.

Known apparatuses for evaluating wetting balances of solder, flux, solder alloy, solder paste (also referred to as cream solder) and so forth provided to lead portions of lead parts, lead and electrode portions of surface mounted parts, or land portions on printed circuit boards include an apparatus disclosed in Japanese Laid-Open Patent Publication No. H7-72064, and an apparatus specified based thereon by Standards of Electronic Industries Association of Japan (EIAJ) ET-7404, "Method for Testing Solderability of Surface Mounted Parts Using Solder Paste (Equilibrium Method)". The solderability testing apparatuses disclosed in these documents are suitable for solderability testing based on the equilibrium method.

Figure 1:
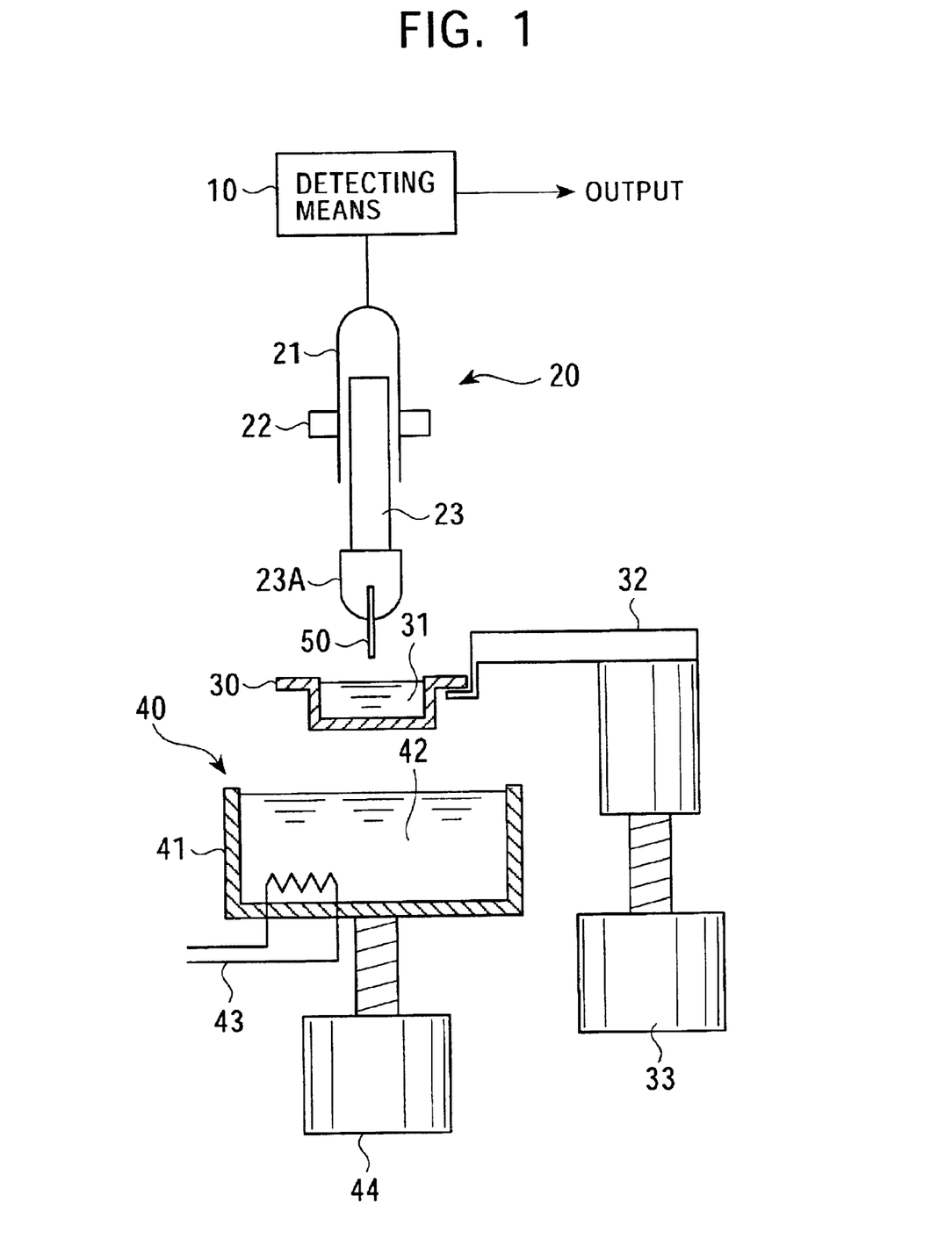
FIG. 1 is a schematic drawing of the solderability testing apparatus.

As schematically shown in FIG. 1, the solderability testing apparatus specifically comprises a sample parts holding means 20, an external force detection means 10 for supporting such sample parts holding means 20, a solder paste container 30, and a heating means 40. The external force detection means 10 has a load cell (high-sensitivity load sensor). The solder paste container 30 contains a solder paste 31 which is internally added with a flux. The sample parts holding means 20 comprises a sample parts holding member 23 for holding a sample (or standard test piece) 50, an expansion sliding portion 21 for supporting such sample parts holding member 23, and an electromagnetic clutch 22 for locking such sliding portion 21. The sliding portion 21 is suspended at the upper end thereof from the external force detection means 10.

The solder paste container 30 is supported by a holder 32, and such holder 32 can ascend or descend, together with the solder paste container 30, with the aid of a stepping motor 33. The heating means 40 has a solder bath 41 which serves as a heat source. Solder 42 contained in the solder bath 41 is heated by a heater 43 to be brought into a molten state. The temperature of the solder 42 is monitored with a temperature sensor (e.g., thermocouple), not shown, and results of the measurement are fed back to control the heater 43. This allows the molten solder 42 in the solder bath 41 to be kept at a predetermined temperature. By dipping the solder paste container 30 in the solder bath 41 containing the molten solder 42 then successfully heats the solder paste 31 contained in such solder paste container 30 to thereby keep the molten state thereof at a predetermined temperature. The solder bath 41 can be ascend or descend with the aid of the stepping motor 44 provided thereunder.

Figure 6A:
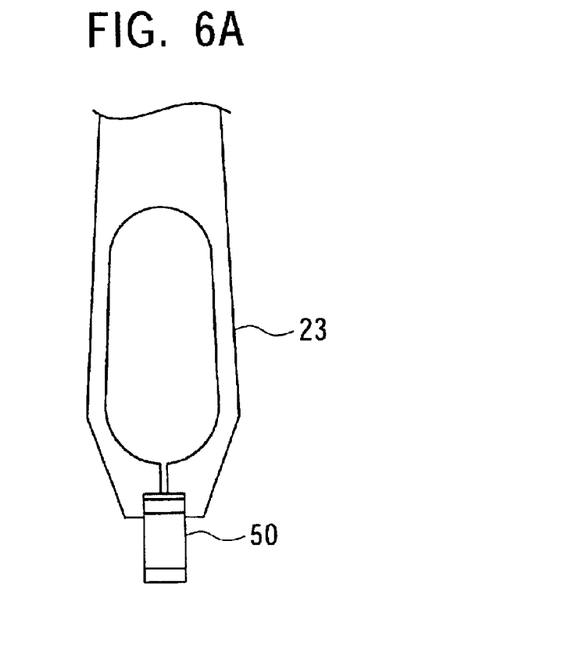
FIG. 6A is a schematic drawing of the sample parts holding member in a state of holding a sample.

FIG. 6A is a partial schematic view of the sample parts holding member 23 in a state of holding a sample 50 (e.g., surface mounted parts). The sample parts holding member 23 of the conventional solderability testing apparatus has been made of all sort of metals which can form structural member (except for those having a melting point of 500° C. or lower, or those possibly act as a solder poison such as zinc and aluminum), which can be typified by steel and stainless steel material.

In the solderability testing, the sample 50 is held by the sample parts holding member 23, the stepping motor 33 is activated so as to raise the holder 32 together with the solder paste container 30 containing the solder paste 31, and the lower end of the sample 50 goes into the solder paste 31 and finally reaches the bottom plane of the solder paste container 30. Thereafter the solder paste container 30 pushes the sample 50 upward while being raised by the ascending holder 32. Thus the sample parts holding member 23 moves upward within the sliding portion 21 of the sample parts holding means 20 as much as the length of ascending path of the sample 50. After the ascending of the holder 32 together with the solder paste container 30 comes to the end, the sliding portion 21 is locked by means of the electromagnetic clutch 22. The lower end of the sample 50 is now in contact with the bottom plane (upper bottom) of the solder paste container 30. The stepping motor 33 is then activated to descend the holder 32 together with the solder paste container 30. Thus the sample 50 is held so that the lower end thereof is dipped in the solder paste 31 to a predetermined depth so as to keep a predetermined gap between such lower end and the upper bottom of the solder paste container 30.

Since the external force detection means 10 composing the load cell is applied with a load which is ascribable to the weights of the sample parts holding means 20 and the sample 50, so that such load is canceled as a tare so as to attain a load-zero status.

Then the stepping motor 44 is activated to raise the solder bath 41. This allows the solder paste 31 contained in the solder paste container 30 to be quickly heated to a temperature of the molten solder 42 and brought into a molten state. In the melting process of such solder paste 31, acting forces exerted on the sample 50, which are typified by buoyancy attributable to the solder paste 31 and surface tension of the molten solder paste 31, are detected by the load cell which composes the external force detection means 10, and then output as electric signals.

In the process of soldering, acting forces effecting between the molten solder paste 31 and the sample 50 are considered as two ways; that are acting force $f_1$ ascribable to the surface tension of the solder paste 31; and buoyancy $f_2$ from the molten solder paste 31, while ignoring the weight of adhered solder. The acting force $f_1$ and buoyancy $f_2$ can be expressed by the following equations (1) and (2), respectively, where force (tension) directed downward is defined as positive force.

$$f_1 = \gamma l \cos \Theta) \tag{1}$$

$$f_2 = -\rho v g \tag{2}$$

, where, meanings of γ, Θ, l, ρ, v and g are respectively as follows:

γ=boundary tension between molten solder paste and flux;
Θ=contact angle of molten solder paste with sample;
l=outer peripheral length of a sample measured at contact plane with molten solder paste;
ρ=density of molten solder paste;
v=volume of displaced molten solder paste; and
g=gravitational acceleration.

When heating of the solder paste 31 starts, the surface of the sample 50 starts to be wet with the flux preliminarily mixed into the solder paste 31, where the flux is responsible for removing oxide film or foreign matters from the surface of the sample 50 to thereby clean such surface of the sample 50.

Then the solder paste 31 starts to melt, buoyancy ascribable to such molten solder paste 31 starts to effect, and wetting with such solder paste 31 also starts when the temperature of the sample reaches a predetermined level. The force F exerted on the sample 50 herein is expressed as an equation below.

$$F=f_1+f_2=\gamma l \cos \Theta - \rho v g$$

Figure 5:
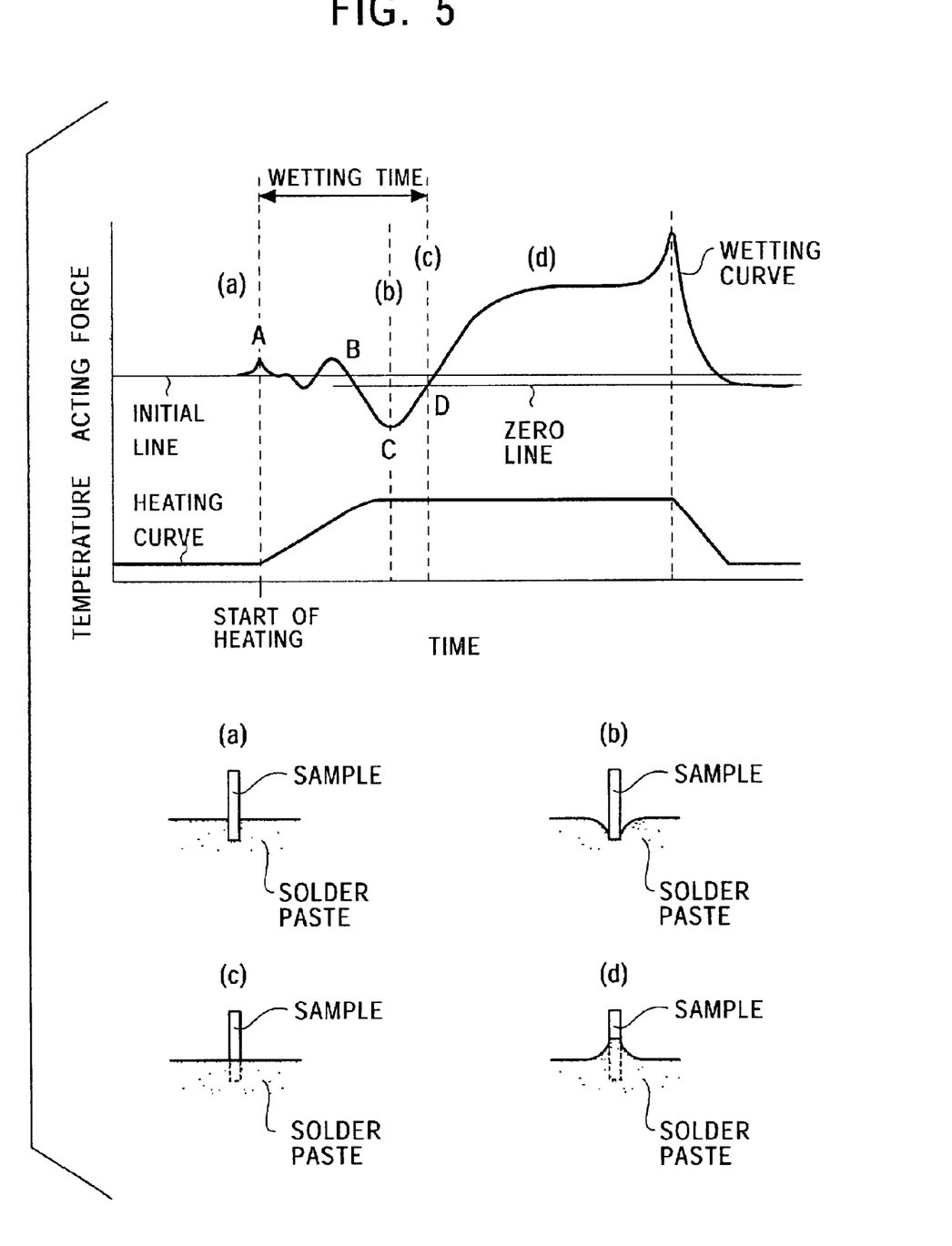
FIG. 5 is a drawing for explaining time-dependent changes in the acting force applied by the molten solder paste onto the sample (wetting curve), time-dependent changes in the heating process, and wetting statuses of a sample.

Time-course of such acting force (expressed by a wetting curve), time-course of the heating process, and wetting status of the sample 50 are shown in FIG. 5. Heating of the sample 50 immersed into the solder paste 31 starts at a point A in FIG. 5. Status of the sample 50 and solder paste 31 is expressed with a reference alphabet (a) in FIG. 5.

After complicated processes between points A and B, which include run of the solder paste 31, evaporation of the solvent and wetting of the flux (where the acting force ascribable to surface tension of the flux becomes maximum at the point B), the solder paste 31 starts to melt at such point B. Upon beginning of the melting of the solder paste 31, the buoyancy attributable thereto begins to effect, which is detected as a repulsive force against the sample 50 (a downward force in FIG. 5). Such repulsive force becomes maximum at a point C, and the entire solder paste 31 completes the melting. Also the contact angle between the molten solder paste 31 and the sample 50 reaches maximum as schematically indicated by reference alphabet (b) in FIG. 5 (>90°). By this point of time, a condition for wetting of the surface of the sample 50 with the molten solder paste 31 is already satisfied, so that the wetting starts. The acting force (referred to as tension hereinafter) ascribable to the surface tension of the molten solder paste 31 increases at the point C and thereafter, and suction force for the sample 50 (upward force in FIG. 5) is begun to be detected. The acting force F becomes zero at a point D, where the buoyancy and tension are kept in balance with each other.

The contact angle attained at this point of time is 90° as specifically indicated by reference alphabet (c) in FIG. 5. The contact angle then decreases below 90° at the point D and thereafter, where the molten solder paste 31 creeps up the non-dipped portion of the sample 50 to thereby form a meniscus as specifically indicated by reference alphabet (d) in FIG. 5.

The time period from the start of the heating (the point A) to the point D is referred to as wetting time $t_w$ (zero-cross time). The point D can be obtained approximately as an intersection of the zero line and wetting curve shown in FIG. 5. It is to be noted now that load difference between the zero line and the initial line indicating the zero-load status before the testing is started represents the weight of the solder paste bonding (remaining) on the sample 50 at the time point when the testing is completed. The shorter the wetting time $t_w$ is, the better the wetting balance between the solder paste 31 and sample 50 becomes, which indicates better solderability.

Figure 6B:
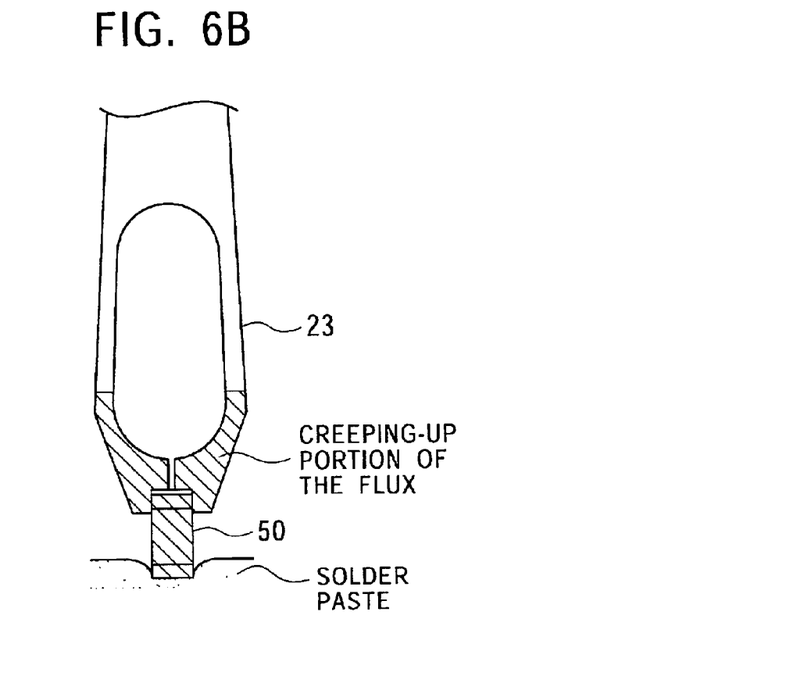
FIG. 6B is a schematic drawing of the sample parts holding member in a state the flux creeps up to the upper portion thereof.
Figure 7:
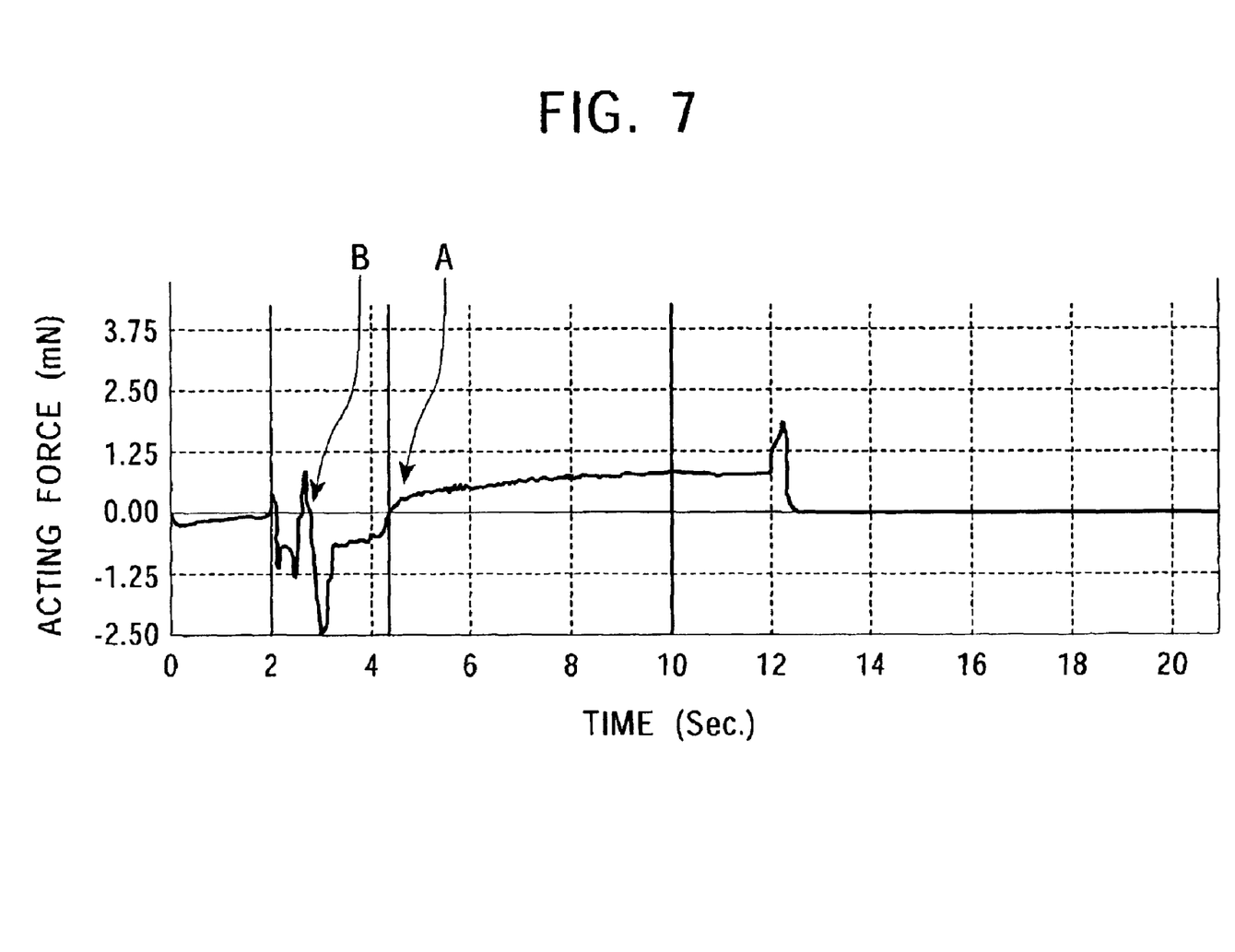
FIG. 7 is a graph showing a wetting curve (of the foregoing part) involving disturbance due to the flux creepage up to the sample parts holding member (corresponded to the state shown in FIG. 6B)

When the heating of the solder paste 31 begins, wetting of the surface of the sample 50 with the flux mixed into such solder paste 31 begins. More specifically, the flux creeps upward on the surface of the sample 50, instantaneously invades into the micro-gap between the sample 50 and sample holding portion of the sample parts holding member 23, and may even instantaneously reaches the top portion of the sample parts holding member 23. Such status is schematically illustrated in FIG. 6B, where the portion having the flux crept thereon is shown with hatching for easy understanding. This is attributable to the surface tension of the flux. Once such creeping-up of the flux such that reaching the top portion of the sample parts holding member occurs, the load cell detects surface tension and weight of the flux excessively applied thereto and also detects acting force caused by abrupt movement of the flux, which adversely affect detection result of the acting force (disturbance of the wetting curve) to a considerable degree. Or acting force ascribable to the surface tension of the flux can heavily affect the acting force detected by the load cell. The load cell which composes the external force detection means 10 is designed to detect extremely small force (in the order of several mN(Newton) to ten and several mN). So that such invasion and creeping-up of the flux into or onto the unnecessary portions will prevent the load cell composing the external force detection means 10 from precisely detecting the acting force exerted on the sample 50. Such wetting of the flux will even be more abrupt and rapid as compared with that of the solder paste, so that it becomes difficult to determine wetting time $t_w$. A wetting curve for an exemplary case with such event is shown in FIG. 7.

Figure 8:
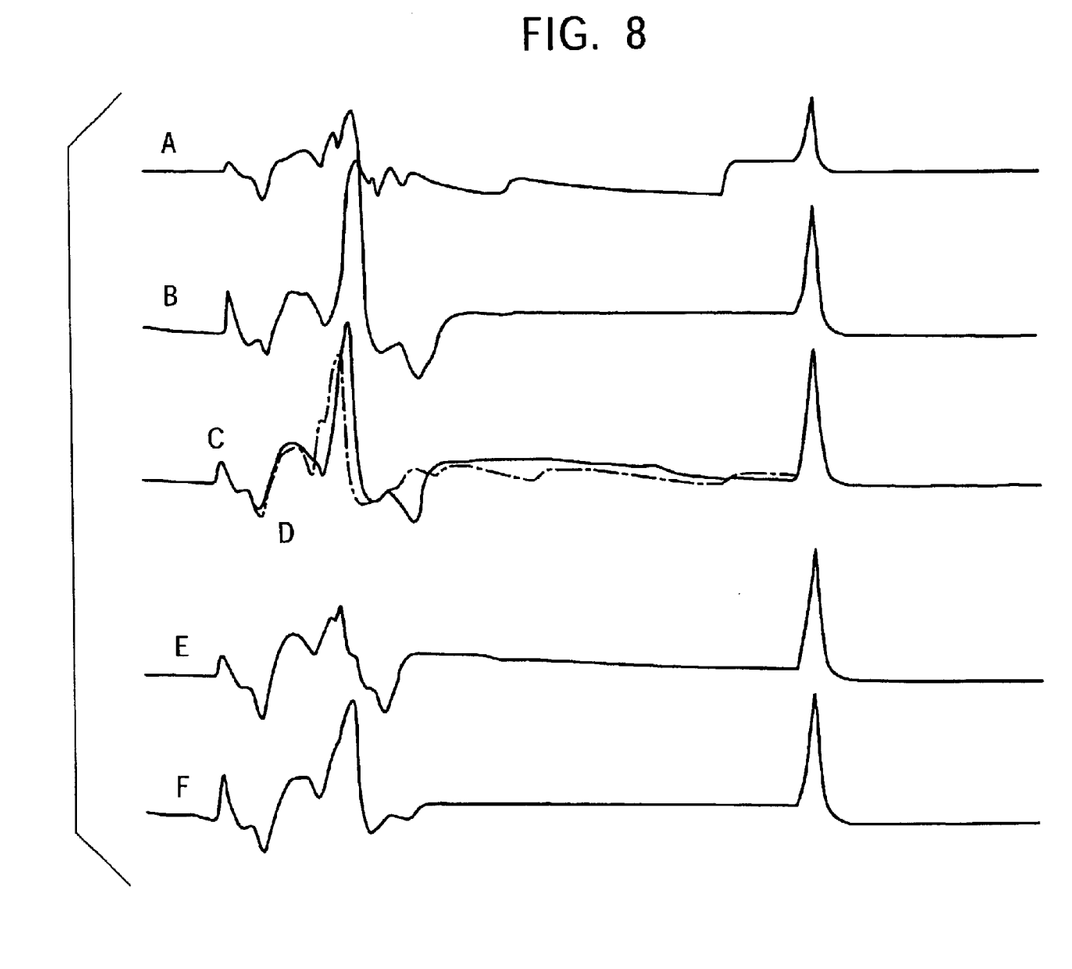
FIG. 8 is a graph showing exemplary wetting curves (of the foregoing lead-free solder paste) involving disturbance due to the flux creepage up to the sample parts holding member (corresponded to the state shown in FIG. 6B).

The wetting $t_w$ can generally be estimated by personal-computer-assisted analysis of detected output of the external force detection means 10 (more specifically, load cell). However for the case shown in FIG. 7, the personal-computer-assisted analysis will determine a point B as a wetting time $t_w$ (zero-cross time), while an actual one should be determined as a point A, which erroneously shortens the observed wetting time $t_w'$ than the actual wetting time $t_w$. Wetting curves obtained for the case with such phenomenon lacks reproducibility and consistency as typically shown in FIG. 8, which makes it extremely difficult to resolve such problem in the analysis of the wetting time on the software basis. FIG. 8 shows six wetting curves, and two out of six are expressed in an overlapped manner.

SUMMARY OF THE INVENTION

It is therefore an aspect of the present invention to provide a solderability testing apparatus and a solderability testing method, both of which can completely prevent the unnecessary flux wetting such that the flux invades upwardly into the gap between the sample and sample parts holding member, or even creeps up to the top portion of the sample parts holding member, and can ensure precise measurement of the wetting time particularly for the case that small-sized SMDs (Surface Mounted Devices) such as those of 0603 type or 1005 type are tested.

A solderability testing apparatus according to first and second aspects of the present invention, and a solderability testing method according to first to third aspects of the present invention are essentially based on the Standards of Electronic Industries Association of Japan (EIAJ) ET-7404, "Method for Testing Solderability of Surface Mounted Parts Using Solder Paste (Equilibrium Method)".

The solderability testing apparatus according to a first aspect of the present invention for attaining the foregoing aspect is such that comprises: (A) a sample parts holding means having a sample parts holding member for holding a sample; (B) an external force detection means for supporting such sample parts holding means; (C) a solder paste container for containing a solder paste which is internally added with a flux; and (D) a heating means for heating the solder paste; wherein such apparatus has a flux wetting preventive layer at least on the surface of a sample holding portion of the sample parts holding member.

A solderability testing method according to a first aspect of the present invention for attaining the foregoing object is such that using a solderability testing apparatus comprises: (A) a sample parts holding means having a sample parts holding member for holding a sample; (B) an external force detection means for supporting such sample parts holding means; (C) a solder paste container for containing a solder paste which is internally added with a flux; and (D) a heating means for heating the solder paste; such apparatus having a flux wetting preventive layer at least on the surface of a sample holding portion of the sample parts holding member; wherein such method comprises a step of heating and melting the solder paste using a heating means while keeping a part of a sample, which is held by a sample parts holding member, being dipped therein, and measuring time-dependent changes in the acting force effected between the molten solder paste and the sample using the external force detection means.

In the solderability testing apparatus or solderability testing method according to the first aspect of the present invention, the flux wetting preventive layer may be provided at least on the surface of a sample holding portion of the sample parts holding member, or may be provided on the most or entire surface of the sample parts holding member. More specifically, the flux wetting preventive layer may typically be formed on the surface of the sample holding portion of the sample parts holding member and the portion above thereof (portion onto which the flux can creep up).

The solderability testing apparatus according to a second aspect of the present invention for attaining the foregoing object is such that comprises: (A) a sample parts holding means having a sample parts holding member for holding a sample; (B) an external force detection means for supporting such sample parts holding means; (C) a solder paste container for containing a solder paste which is internally added with a flux; and (D) a heating means for heating the solder paste; wherein a sample holding portion of the sample parts holding member is made of a material having a poor wetting balance in respect of the flux.

A solderability testing method according to a second aspect of the present invention for attaining the foregoing object is such that using a solderability testing apparatus comprises: (A) a sample parts holding means having a sample parts holding member for holding a sample; (B) an external force detection means for supporting such sample parts holding means; (C) a solder paste container for containing a solder paste which is internally added with a flux; and (D) a heating means for heating the solder paste; such sample parts holding member having a sample holding portion which is made of a material having a poor wetting balance in respect of the flux, wherein such method comprises a step of heating and melting the solder paste using a heating means while keeping a part of a sample, which is held by a sample parts holding member, being dipped therein, and measuring time-dependent changes in the acting force effected between the molten solder paste and the sample using the external force detection means.

In the solderability testing apparatus or solderability testing method according to the second aspect of the present invention, at least the sample holding portion of the sample parts holding member may be made of a material having a poor wetting balance in respect of the flux, while it is also allowable that the entire portion of the sample parts holding member is made of a material having a poor wetting balance in respect of the flux. It is also preferable to form the sample holding portion of the sample parts holding member with a material having a poor heat conductivity.

In the solderability testing apparatus or solderability testing method according to the first aspect of the present invention, the material composing the flux wetting preventive layer preferably has a contact angle $\overset{\sim}{E}$ to flux of larger than 90°, and such material is preferably selected from polymer material, cermet and ceramic. The polymer material herein preferably has excellent heat resistance, wear-proof property and water repellency, where preferable examples of which include various engineering plastics such as fluorocarbon resin or derivatives thereof (e.g., polytetrafluoroethylene) and polyoxymethylene (POM) resins. The cermet or ceramic herein preferably has excellent water repellency. The cermet refers to a composite material obtained by sintering ceramic and metal powder, or a composite material composed of ceramic, metal and so forth, and examples of which include those in which metal such as iron (Fe), nickel (Ni), cobalt (Co), chromium (Cr), molybdenum (Mo) or the like is combined with silicon (Si), boron (B), various carbides (TiC, ZrC, $B_4C$, WC, SiC, etc.), oxides ($Al_2O_3$, $ZrO_2$, $ThO_2$, etc.) or nitrides (W—N, Mo—N, TaN, B—N, etc.). The ceramic can be exemplified by so-called new ceramics such as alumina, mullite, magnesia, forsterite, zirconia, titania, yttria or the like; vitreous materials such as borosilicate glass, potassium borosilicate glass or the like; quartz glass and phosphosilicate glass.

Possible methods for forming the flux wetting preventive layer depend on materials composing such layer, where examples thereof include such that dipping the sample holding portion of the sample parts holding member (or entire portion thereof if necessary) into solution of a material composing such flux wetting preventive layer, which is followed by drying; such that coating solution of a material composing such flux wetting preventive layer on the portion the flux wetting preventive layer is to be formed, which is followed by drying; such that spraying solution of a material composing the flux wetting preventive layer to a portion the flux wetting preventive layer is to be formed, which is followed by sintering or flame coating if necessary; such that coating (depositing) the material; and such that forming film of a material composing the flux wetting preventive layer on the portion the flux wetting preventive layer is to be formed by physical vapor deposition (PVD) process such as sputtering or vapor deposition, or chemical vapor deposition (CVD) process. It is also allowable to employ direct processing or forming of plastic materials.

In the solderability testing apparatus or solderability testing method according to the second aspect of the present invention, the material composing at least sample holding portion (or the entire portion if necessary) of the sample parts holding member preferably has a contact angle E to flux of larger than 90°, and such material is preferably selected from various engineering plastics such as polymer materials having excellent heat resistance, processability, wear-proof property and strength (e.g., fluorocarbon resin or derivatives thereof typified by polytetrafluoroethylene, and polyoxymethylene resins), and from the foregoing cermet or ceramic.

In the solderability testing apparatus according to the first and second aspects of the present invention, and in the solderability testing method according to the first and second aspects of the present invention (all of which may simply be referred to as "the present invention" hereinafter), the sample parts holding means preferably comprises an expandable sliding portion for supporting the sample parts holding member and an electromagnetic clutch for locking such sliding portion. The sliding portion is preferably suspended at the upper end thereof from the external force detection means; or the sample parts holding member, which is made of a flexible (springy) material, preferably has on the outer periphery thereof a sleeve covering thereof, and is suspended at the upper end of such sleeve or at the sample parts holding member per se from the external force detection means, although the present invention is by no means limited to these constitutions.

In the present invention, the external force detection means can be composed, for example, of a high-sensitivity load sensor such as load cell, or an electronic balance. The solder paste container can specifically be composed of testing jig plate I or II specified in EIAJ ET-7404. The heating means preferably has a heating bath containing liquid metal (e.g., solder bath containing solder, heating bath containing fusible alloy such as Wood's metal), which can ensure a larger contact surface area than a heating plate can.

In the solderability testing method according to the first and second aspects of the present invention (generally referred to as "the solderability testing method of the present invention" hereinafter), the acting force effected between the molten solder paste and the sample is specifically understood as a synthetic force of buoyancy exerted on the sample from the solder in the molten solder paste and the surface tension (tension).

The present invention is applicable to evaluation of solderability of the samples, or solder wetting balance listed below:

(1) lead portion of lead parts;
(2) electrode portion (terminal portion) of surface mounted parts;
(3) land portion provided on printed circuit boards;
(4) flux;
(5) solder alloy (including lead-free solder such as Sn—Cu and Sn—Cu—Ag solders);
(6) solder paste (also referred to as cream solder);
(7) raw materials before being processed into part terminal leads or lead frames, such as wire material (Cu/CP wire), hoop material (to be processed into lead frame, terminal and so forth, and exemplified by 426 alloy, 42 alloy, etc.), steel sheet (tin-plated or zinc-plated steel plate such as tin plate or galvanized steel sheet);
(8) materials obtained by subjecting the materials described above in (7) to various plating processes (evaluation of solder wetting balance of plating chemicals);
(9) evaluation of solderability of films formed using surface treatment apparatuses such as PVD and CVD apparatuses on the materials described above in (7);
(10) performance test of solderability in apparatuses and methods of surface treatment such as PVD and CVD; and
(11) surface treatment materials (BTA, imidazole) other than flux in relation to the solderability.

For the evaluation of (1), (2) or (3), lead part, surface mounted part, printed wiring board, or land portion on such printed wiring board is assumed as the sample. In such cases, it is preferable to use for example a standard solder paste specified by EIAJ ET-7404, or a standard (reference) paste preliminarily defined by the user. When items (1) to (3), and (7) to (10) are to be evaluated, the evaluation preferably follows the solderability testing method according to the first or second aspect of the present invention. Conditions for such testing are preferably in compliance with the recommended testing conditions specified by EIAJ ET-7404, while not being limited thereto.

On the other hand, for the evaluation of item (4), it is preferable to use a copper oxide wire (0.6 mm in diameter) or a reference material defined by the user (e.g., electrodes subjected to lead-free plating with Sn—Cu, Sn, Sn—Ag or the like) as a standard sample, and to prepare the solder paste using a component solder powder specified by EIAJ ET-7404. For the evaluation of items (5), (6) and (11), it is preferable to use a copper oxide wire (0.6 mm in diameter) as a standard sample. When items (4), (5), (6) and (11) are to be evaluated, the evaluation preferably follows the solderability testing method according to the first or second aspect of the present invention.

In the solderability testing methods according to the first and second aspects of the present invention, temperature elevation profile attained in the process in which the solder paste is heated using a heating means to be brought into a molten state (elevation profile of sample temperature) preferably follows the rapid heating profile specified by EIAJ ET-7404, while being not limited thereto.

In the present invention, at least the surface of the sample holding portion of the sample parts holding member has formed thereon the flux wetting preventive layer, or at least the sample holding portion of the sample parts holding member is made of a material having a poor wetting balance, which is advantageous for surely preventing the flux from invading into the gap between the sample and sample holding portion of the sample parts holding member, and eventually from creeping up to the sample parts holding member. This ensures precise measurement of the wetting time.

BRIEF DESCRIPTION OF THE DRAWINGS

The above and other objects, features and advantages of the present invention will become more apparent from the following description of the presently preferred exemplary embodiment of the invention taken in conjunction with the accompanying drawings, in which.

DETAILED DESCRIPTION OF THE PREFERRED EMBODIMENTS

The present invention will be described referring to embodiments of the present invention (simply referred to as embodiment, hereinafter).

(Embodiment 1)

The embodiment 1 relates to the solderability testing apparatus and solderability testing method according to the first aspect of the present invention. Constitution of the solderability testing apparatus of the embodiment 1 can be almost similar to that of the conventional solderability testing apparatus previously explained referring to FIG. 1, so that detailed description thereof will be omitted.

Figure 2:
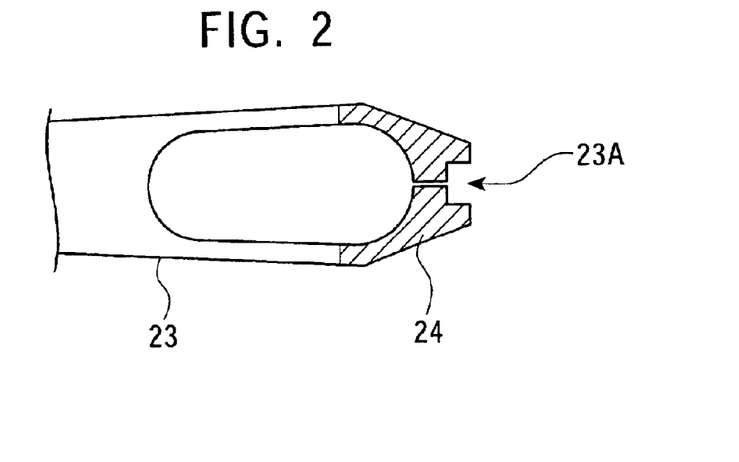
FIG. 2 is a partial schematic view of the sample parts holding member of the solderability testing apparatus according to the present invention.

A partial schematic view of the sample parts holding member 23 of the solderability testing apparatus of the embodiment 1 is shown in FIG. 2. The sample parts holding member 23 is made of a steel material or stainless steel, and has the flux wetting preventive layer 24 comprising a flux creepage preventive agent at least on the surface of the sample holding portion 23A thereof. Now the drawing shows the flux wetting preventive layer 24 with hatching for easy understanding. Specifically, the flux wetting preventive layer 24 was formed by spraying SFCOAT SIF-200 AEROSOL (product of Seimi Chemical Co., Ltd., major component: fluorocarbon resin, available as an isopropanol solution) onto the surface of the sample holding portion 23A and around thereof of the sample parts holding member 23, and then drying at 200° C. using an industrial drier. Such spraying and baking finish were repeated three times to thereby form the flux wetting preventive layer 24 on the sample holding portion 23A and around thereof of the sample parts holding member 23.

Thus fabricated sample parts holding member 23 was attached to the solderability testing apparatus shown in FIG. 1. The sample 50 employed herein was a chip-type tantalum capacitor having 42-alloy terminals with Sn-plated surface in a size of 6.2 mm×5.8 mm×1.2 mm (product of Nichicon Corporation), or an 1005-type chip resistor having terminals with solder plating on Ag—Pd baked (thick-film) electrodes (product of Taiyo Electric Co., Ltd.). The solder paste for the testing employed herein was a standard solder paste specified in the EIAJ ET-7404 (product of Tarutin Kester Co., Ltd.). The testing employed the testing conditions specified in the EIAJ ET-7404 (angle of dipping: horizontal, dipping direction: 1A); rapid seating profile specified in EIAJ ET-7404 as the temperature elevation profile (elevation profile of sample temperature) attained when the solder paste 31 is heated to a molten state using the heating means 40; testing jig plate II specified in the EIAJ ET-7404 as the solder paste container 30; and the depth of dipping of 0.1 mm to 0.2 mm (depending on part size). Specific procedures of the solderability testing are the same with those explained above in the Description of the Related Art.

Figure 3:
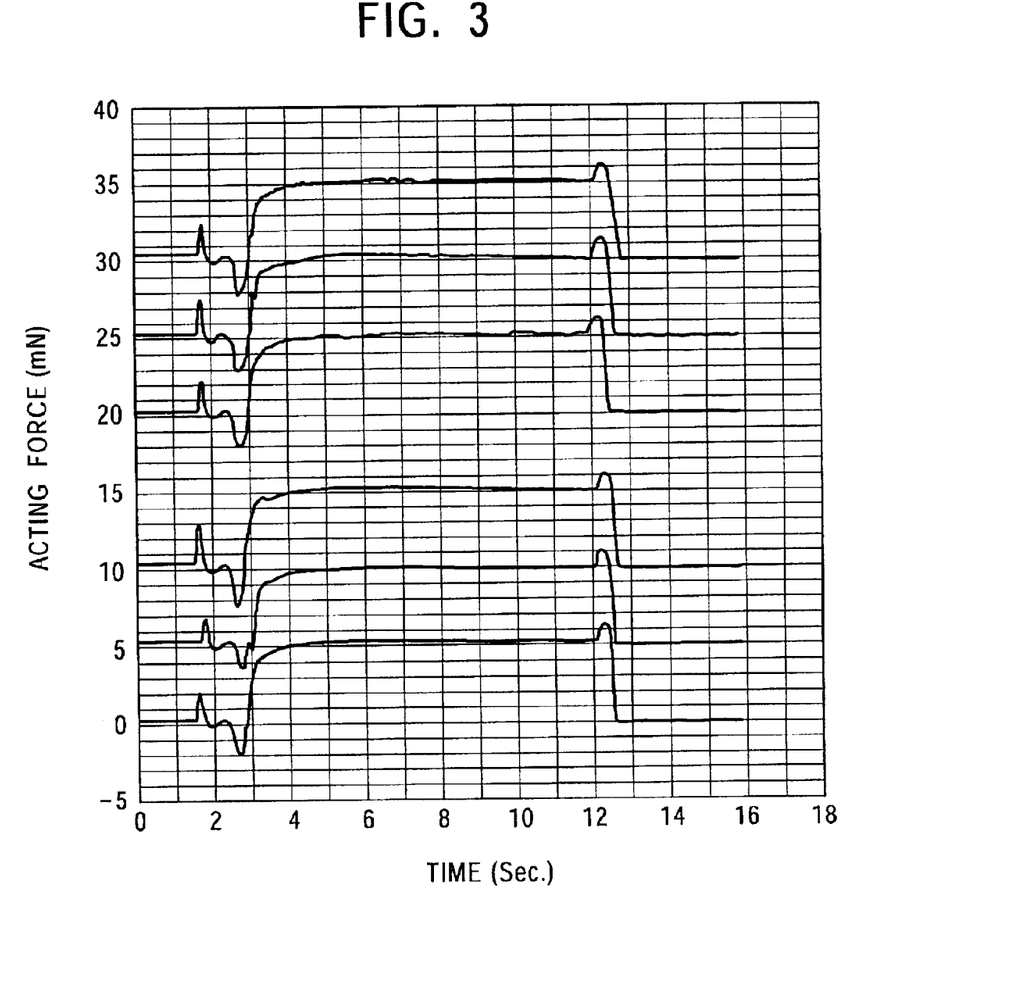
FIG. 3 is a graph showing exemplary wetting curves of a terminal of a 1005-type part subjected to lead-free surface treatment (Sn—Cu plating) according to Embodiment 1 of the invention.
Figure 4:
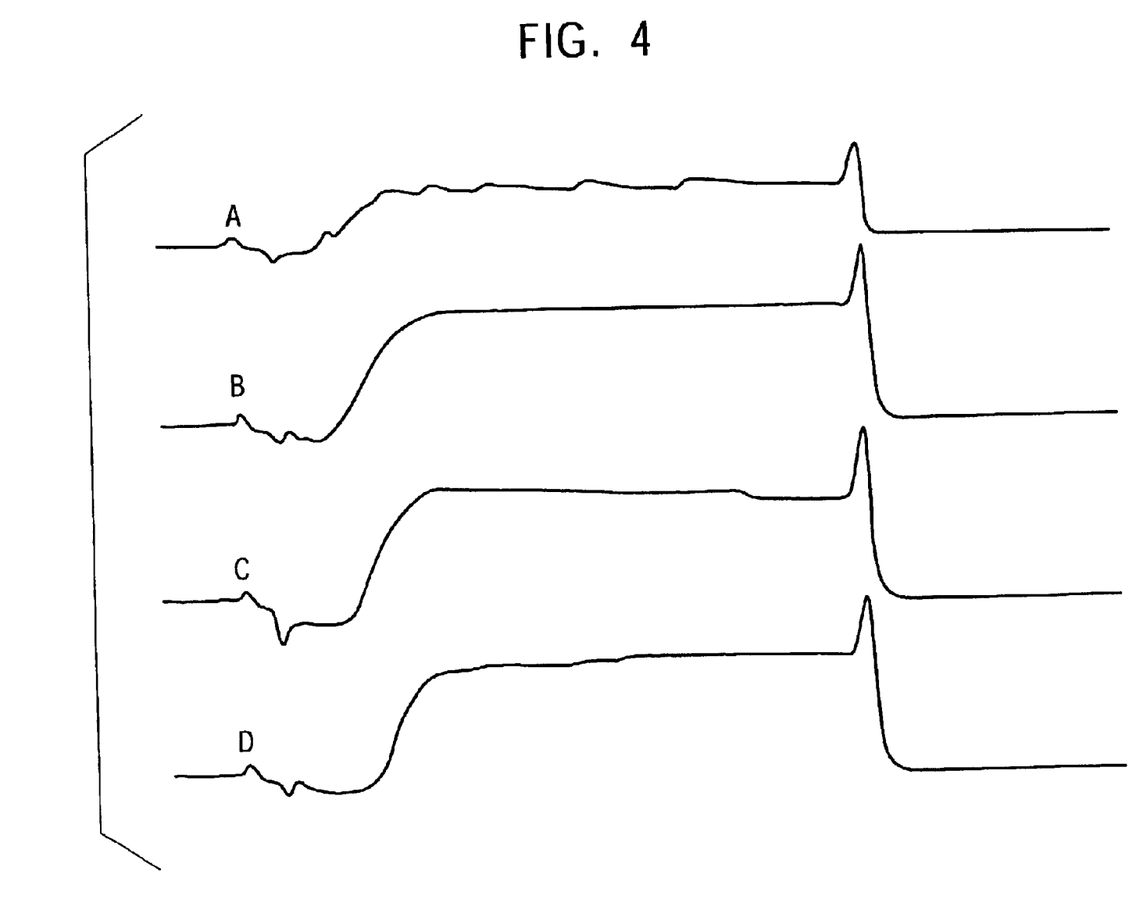
FIG. 4 is a graph showing exemplary wetting curves of the lead-free solder paste (Sn—3.5Ag—0.5Cu) according to Embodiment 1 of the invention.

Thus obtained wetting curves are shown in FIGS. 3 and 4. FIGS. 3 and 4 show wetting curves observed at 6 points and 4 points, respectively. Observation of the sample holding portion 23A of the sample parts holding member 23 after the testing showed almost no flux creepage onto such sample holding portion 23A. It was also found that the wetting curves were obtained in a highly consistent manner, which ensured precise measurement of the wetting time.

(Embodiment 2)

The embodiment 2 also relates to the solderability testing apparatus and solderability testing method according to the first aspect of the present invention. While the sample parts holding member 23 in the embodiment 2 is also made of a material same as that for the embodiment 1, the entire surface of which has formed thereon the flux wetting preventive layer 24 comprising a fluorocarbon resin derivative. More specifically, the entire portion of the sample parts holding member 23 was dipped in an isopropanol solution or perfluorocarbon solution of a fluorocarbon resin derivative (content of the fluorocarbon resin derivative of 0.2 to 1%), and the solution was then dried using a hair drier to thereby form the flux wetting preventive layer 24. Dipping only the sample holding portion 23A (and around thereof) of the sample parts holding member 23 into such solution and then drying thereof can form the flux wetting preventive layer only on the surface of the sample holding portion 23A and around thereof of the sample parts holding member 23. It is also allowable to coat using a brush or the like such solution onto the entire surface of the sample parts holding member 23 or onto the sample holding portion 23A (and around thereof) of the sample parts holding member 23, in place of dipping into such solution, and then dry such solution. Such dipping into or coating of such solution may be repeated twice or more times.

Thus obtained sample parts holding member 23 was attached to the solderability testing apparatus shown in FIG. 1, and then subjected to the solderability testing similarly to the embodiment 1. Observation of the sample holding portion 23A of the sample parts holding member 23 after the testing showed almost no flux creepage onto such sample holding portion 23A. It was also found that the wetting curves were obtained in a highly consistent manner, which ensured precise measurement of the wetting time.

(Embodiment 3)

The embodiment 3 also relates to the solderability testing apparatus and solderability testing method according to the first aspect of the present invention. While the sample parts holding member 23 in the embodiment 3 is also made of a material same as that for the embodiment 1, the member has formed thereon the flux wetting preventive layer 24 comprising a fluorocarbon resin derivative. More specifically, a film of the flux wetting preventive layer 24 was formed on the sample holding portion 23A and around thereof of the sample parts holding member 23 by sputtering using a polytetrafluoroethylene target.

Thus obtained sample parts holding member 23 was attached to the solderability testing apparatus shown in FIG. 1, and then subjected to the solderability testing similarly to the embodiment 1. Observation of the sample holding portion 23A of the sample parts holding member 23 after the testing showed almost no flux creepage onto such sample holding portion 23A. It was also found that the wetting curves were obtained in a highly consistent manner, which ensured precise measurement of the wetting time.

(Embodiment 4)

The embodiment 4 also relates to the solderability testing apparatus and solderability testing method according to the first aspect of the present invention. While the sample parts holding member 23 in the embodiment 4 is also made of a material same as that for Embodiment 1, the member has formed thereon the flux wetting preventive layer 24 comprising a ceramic. More specifically, alumina was applied by ceramic coating and then baked to thereby form the flux wetting preventive layer 24 onto the sample holding portion 23A and around thereof of the sample parts holding member 23.

Thus obtained sample parts holding member 23 was attached to the solderability testing apparatus shown in FIG. 1, and then subjected to the solderability testing similarly to Embodiment 1. Observation of the sample holding portion 23A of the sample parts holding member 23 after the testing showed almost no flux creepage onto such sample holding portion 23A. It was also found that the wetting curves were obtained in a highly consistent manner, which ensured precise measurement of the wetting time.

(Embodiment 5)

The embodiment 5 also relates to the solderability testing apparatus and solderability testing method according to the first aspect of the present invention. While the sample parts holding member 23 in Embodiment 5 is also made of a material same as that for Embodiment 1, the member has formed thereon the flux wetting preventive layer 24 comprising a cermet. More specifically, the flux wetting preventive layer 24 comprising cermet was formed on the sample holding portion 23A and around thereof of the sample parts holding member 23 by sputtering using SiC and TaN targets.

Thus obtained sample parts holding member 23 was attached to the solderability testing apparatus shown in FIG. 1, and then subjected to the solderability testing similarly to the embodiment 1. Observation of the sample holding portion 23A of the sample parts holding member 23 after the testing showed almost no flux creepage onto such sample holding portion 23A. It was also found that the wetting curves were obtained in a highly consistent manner, which ensured precise measurement of the wetting time.

In such embodiments 1 to 5, composing the flux wetting preventive layer 24 with a material having a low heat conductivity can prevent heat supplied from the heating means 40 to the sample 50 from conducting (dissipating) toward the sample parts holding member 23, which successfully raises accuracy in the temperature control of the solder paste 31, and reduces a ratio of temperature elevation time included in the wetting time (delay in the temperature elevation), which ensures more precise measurement of the wetting time. Heat conductivity of a material composing such flux wetting preventive layer 24 is typically 1/100 or below of that for metal (Ni), that is 0.2 to 1.0 W·m$^{-1}$·K$^{-1}$ (300K).

(Embodiment 6)

The embodiment 6 relates to the solderability testing apparatus and solderability testing method according to the second aspect of the present invention. Constitution of the solderability testing apparatus of the embodiment 6, except for the constitution of the sample parts holding member 23, can be almost similar to that of the conventional solderability testing apparatus previously explained referring to FIG. 1, so that detailed description thereof will be omitted.

In the embodiment 6, the sample parts holding member 23 similar to that shown in FIG. 2 was obtained by machining a block of fluorocarbon resin (more specifically, polytetrafluorotehylene).

Thus obtained sample parts holding member 23 was attached to the solderability testing apparatus shown in FIG. 1, and then subjected to the solderability testing similarly to the embodiment 1. Observation of the sample holding portion 23A of the sample parts holding member 23 after the testing showed almost no flux creepage onto such sample holding portion 23A. It was also found that the wetting curves were obtained in a consistent manner, which ensured precise measurement of the wetting time. It was also confirmed that composing the sample parts holding member 23 with such fluorocarbon resin prevent heat supplied from the heating means 40 to the sample 50 from conducting (dissipating) toward the sample parts holding member 23, which successfully raises accuracy in the temperature control of the solder paste 31, and reduces a ratio of temperature elevation time included in the wetting time (delay in the temperature elevation), which ensures more precise measurement of the wetting time. In general, heat conductivity of a material composing at least the sample holding portion of the sample parts holding member is typically 1/100 or below of that for metal (Ni), that is 0.2 to 1.0 W·m$^{-1}$·K$^{-1}$ (300K).

It is now also allowable to fabricate the sample holding portion 23A (a portion expressed by the hatching in FIG. 2, for example) of the sample parts holding member 23 with a fluorocarbon resin (more specifically, polytetrafluoroethylene), to fabricate other portions of the sample parts holding member 23 with other material (steel material or stainless steel), and to assemble these portions to thereby obtain the sample parts holding member 23.

Although the invention has been described referring to Preferred Embodiments, the present invention is by no means limited thereto. It is therefore to be understood that any constitutions of the solderability testing apparatus and testing conditions for the solderability testing method described in the Preferred Embodiments can properly be modified.

What is claimed is:

1. A solderability testing apparatus comprising:
   a sample parts holding means having a sample parts holding member with a sample holding portion for holding a sample;
   an external force detection means for supporting said sample parts holding means;
   a solder paste container for containing a solder paste which is internally added with a flux; and
   a heating means for heating the solder paste;
   wherein said apparatus has a flux wetting preventive layer at least on a surface of a sample holding portion of the sample parts holding member.

2. The solderability testing apparatus as claimed in claim 1, wherein a material composing the flux wetting preventive layer has a contact angle È to flux of larger than 90°.

3. The solderability testing apparatus as claimed in claim 2, wherein the material composing the flux wetting preventive layer is a fluorocarbon resin.

4. The solderability testing apparatus as claimed in claim 2, wherein the material composing the flux wetting preventive layer is cermet or ceramic.

5. A solderability testing apparatus comprising:
   a sample parts holding means having a sample parts holding member for holding a sample;
   an external force detection means for supporting said sample parts holding means;
   a solder paste container for containing a solder paste which is internally added with a flux; and
   a heating means for heating the solder paste;
   wherein at least a sample holding portion of the sample parts holding member is made of a material having a poor wetting balance in respect of the flux.

6. The solderability testing apparatus as claimed in claim 5, wherein a material composing the sample holding portion of the sample parts holding member has a contact angle È to flux of larger than 90°.

7. The solderability testing apparatus as claimed in claim 6, wherein the material composing the flux wetting preventive layer is a fluorocarbon resin.

8. The solderability testing apparatus as claimed in claim 6, wherein the material composing the flux wetting preventive layer is cermet or ceramic.

9. A solderability testing method using a solderability testing apparatus, said apparatus comprising:
   a sample parts holding means having a sample parts holding member with a sample holding portion for holding a sample;
   an external force detection means for supporting said sample parts holding means;
   a solder paste container for containing a solder paste which is internally added with a flux; and
   a heating means for heating the solder paste;
   said apparatus having a flux wetting preventive layer at least on a surface of a sample holding portion of the sample parts holding member;
   wherein said method comprises a step of heating and melting the solder paste using the heating means while keeping a part of a sample, which is held by the sample parts holding member, being dipped therein, and measuring time-dependent changes in the acting force effected between the molten solder paste and the sample using the external force detection means.

10. The solderability testing method as claimed in claim 9, wherein a material composing the flux wetting preventive layer has a contact angle È to flux of larger than 90.

11. The solderability testing method as claimed in claim 10, wherein the material composing the flux wetting preventive layer is a fluorocarbon resin.

12. The solderability testing method as claimed in claim 10, wherein the material composing the flux wetting preventive layer is cermet or ceramic.

13. A solderability testing method using a solderability testing apparatus, which apparatus comprising:
   a sample parts holding means having a sample parts holding member for holding a sample;
   an external force detection means for supporting said sample parts holding means;
   a solder paste container for containing a solder paste which is internally added with a flux; and
   a heating means for heating the solder paste,
   said apparatus having a flux wetting preventive layer at least on the surface of a sample holding portion of the sample parts holding member;
   said sample parts holding member sample holding portion being made of a material having a poor wetting balance in respect of the flux,
   wherein said method comprises a step of heating and melting the solder paste using the heating means while keeping a part of a sample, which is held by the sample parts holding member, being dipped therein, and measuring time-dependent changes in the acting force effected between the molten solder paste and the sample using the external force detection means.

14. The solderability testing method as claimed in claim 13, wherein a material composing the sample holding portion of the sample parts holding member has a contact angle È to flux of larger than 90°.

15. The solderability testing method as claimed in claim 14, wherein the material composing the flux wetting preventive layer is a fluorocarbon resin.

16. The solderability testing method as claimed in claim 14, wherein the material composing the flux wetting preventive layer is cermet or ceramic.

* * * * *